US012576260B2

(12) United States Patent
Dombrowski et al.

(10) Patent No.: US 12,576,260 B2
(45) Date of Patent: Mar. 17, 2026

(54) DISINFECTING CAP FOR OPEN FEMALE LUER DEVICES

(71) Applicant: Solventum Intellectual Properties Company, Maplewood, MN (US)

(72) Inventors: Alan R. Dombrowski, Woodbury, MN (US); John C. Detloff, San Diego, CA (US)

(73) Assignee: Solventum Intellectual Properties Company, Maplewood, MN (US)

( * ) Notice: Subject to any disclaimer, the term of this patent is extended or adjusted under 35 U.S.C. 154(b) by 211 days.

(21) Appl. No.: 18/522,616

(22) Filed: Nov. 29, 2023

(65) Prior Publication Data

US 2024/0091520 A1     Mar. 21, 2024

Related U.S. Application Data

(63) Continuation of application No. 17/088,756, filed on Nov. 4, 2020, now abandoned, which is a continuation of application No. 16/466,078, filed as application No. PCT/US2017/063944 on Nov. 30, 2017, now Pat. No. 10,828,483.

(Continued)

(51) Int. Cl.
| | |
|---|---|
| *A61M 39/16* | (2006.01) |
| *A61L 2/00* | (2006.01) |
| *A61M 39/20* | (2006.01) |
| *B29C 33/44* | (2006.01) |
| *B29C 37/00* | (2006.01) |

(Continued)

(52) U.S. Cl.
CPC ......... *A61M 39/162* (2013.01); *A61L 2/0088* (2013.01); *A61M 39/20* (2013.01); *B29C 33/44* (2013.01); *B29C 37/0014* (2013.01); *B29C 45/2618* (2013.01); *B29C 45/4407* (2013.01); *B29C 2045/4492* (2013.01)

(58) Field of Classification Search
CPC ........... A61M 39/162; B29C 2043/024; B29C 45/2618; B29C 33/44; B29C 37/0014; B29C 45/4407; B29C 2045/4492
See application file for complete search history.

(56) References Cited

U.S. PATENT DOCUMENTS

| | | |
|---|---|---|
| 7,559,530 B2 | 7/2009 | Korogi et al. |
| 8,617,482 B2 | 12/2013 | Tryggvason et al. |

(Continued)

FOREIGN PATENT DOCUMENTS

| | | |
|---|---|---|
| CN | 102065946 A | 5/2011 |
| JP | 2002515311 A | 5/2002 |

(Continued)

OTHER PUBLICATIONS

China National Intellectual Property Administration Search Report for CN201780076187_5, 2 pgs.

(Continued)

*Primary Examiner* — John J DeRusso

(57) ABSTRACT

Disclosed is a cap configured for removable attachment a medical device. The cap has a body with an opening, a bottom, and a chamber defined between the opening and the bottom. The cap has a wall of the chamber comprising a thread originating proximate the opening and extending into the chamber by a height. The height of the thread increases as a function of increasing distance from the opening. A liquid disinfectant is contained within the chamber.

14 Claims, 8 Drawing Sheets

Related U.S. Application Data

(60) Provisional application No. 62/431,901, filed on Dec. 9, 2016.

(51) Int. Cl.
   B29C 45/26     (2006.01)
   B29C 45/44     (2006.01)

(56)                References Cited

U.S. PATENT DOCUMENTS

| | | |
|---|---|---|
| 8,622,995 B2 | 1/2014 | Ziebol et al. |
| 10,828,483 B2 | 11/2020 | Dombrowski et al. |
| 2003/0181849 A1 | 9/2003 | Castellanos |
| 2004/0261872 A1 | 12/2004 | Mermet |
| 2005/0228362 A1 | 10/2005 | Vaillancourt |
| 2009/0008393 A1 | 1/2009 | Howlett et al. |
| 2009/0062766 A1 | 3/2009 | Howlett et al. |
| 2010/0050351 A1 | 3/2010 | Colantonio et al. |
| 2010/0063482 A1 | 3/2010 | Mansour et al. |
| 2011/0265825 A1 | 11/2011 | Rogers et al. |
| 2011/0314619 A1 | 12/2011 | Schweikert |
| 2013/0197485 A1 | 8/2013 | Gardner et al. |
| 2014/0366914 A1 | 12/2014 | Kerr et al. |
| 2015/0126942 A1 | 5/2015 | Lopez et al. |
| 2016/0317798 A1 | 11/2016 | Lopez et al. |
| 2017/0000998 A1 | 1/2017 | Guala |
| 2017/0028187 A1 | 2/2017 | Mansour et al. |
| 2017/0050012 A1 | 2/2017 | Alpert et al. |

FOREIGN PATENT DOCUMENTS

| | | |
|---|---|---|
| JP | 2015521089 A | 7/2015 |
| WO | 1999059672 A2 | 11/1999 |
| WO | 2006019782 A2 | 2/2006 |
| WO | 2010002808 A1 | 1/2010 |
| WO | 2011066586 A1 | 6/2011 |
| WO | 2013066285 A1 | 5/2013 |
| WO | 2013184716 A1 | 12/2013 |

OTHER PUBLICATIONS

International Search report for PCT International Application No. PCT/US2017/063944, mailed on Apr. 9, 2018, 5 pages.

DISINFECTING CAP FOR OPEN FEMALE LUER DEVICES

CROSS-REFERENCE TO RELATED APPLICATIONS

This application is a continuation of U.S. application Ser. No. 17/088,756, filed Nov. 4, 2020, which is a continuation of U.S. application Ser. No. 16/466,078, filed Jun. 3, 2019, issued as U.S. Pat. No. 10,828,483, which is a national stage filing under 35 U.S.C. 371 of PCT/US2017/063944, filed Nov. 30, 2017, which claims the benefit of U.S. Provisional Application No. 62/431,901, filed Dec. 9, 2016, the disclosures of which are incorporated by reference in their entirety herein.

TECHNICAL FIELD

This application relates to disinfecting caps for open female luer devices and methods of making such caps.

BACKGROUND

Presently, open female luer (OFL) devices such as stopcocks and dialysis catheters are covered between use by end caps known as "dead" enders. These caps are provided sterile, and only cover the OFL device to prevent contamination. These caps are deficient in that they do not provide active disinfection of the face and periphery of the OFL device, since the luer can be contaminated during handling and administration of medications.

BRIEF SUMMARY

Some embodiments are directed to a cap configured for removable attachment to an open female luer device having an open distal end and a contacting surface. The cap includes a body comprising an opening configured to receive the female luer device, a bottom, and a chamber defined between the opening and the bottom. The chamber is configured to hold a liquid disinfectant. A male post is disposed in the chamber and dimensioned to receive the female luer device. The male post projects from the bottom towards the opening and comprises a taper corresponding to a taper of the female luer device. A wall of the chamber comprises a thread originating proximate the opening and extending into the chamber. At least a portion of the thread has a height that increases as a function of increasing distance from the opening. A movable piston is positioned about the male post. The movable piston comprises a central opening dimensioned to provide an interference fit with the male post. The piston also comprises a top region configured to form a seal with an inner surface of the open distal end of the female luer device. The piston further comprises a flexible circumferential skirt dimensioned to contact the wall of the chamber.

In other embodiments, a cap includes a body comprising an opening, a bottom, and a chamber defined between the opening and the bottom. The chamber is configured to hold a liquid disinfectant. A male post extends from the bottom towards the opening of the body. A wall of the chamber comprises a thread originating proximate the opening and extending into the chamber. At least a portion of the thread has a height that increases as a function of increasing distance from the opening.

Further embodiments are directed to a method of molding a cap comprising a chamber with a thread having a variable thread height. The method involves providing a mold comprising at least a first side and a second side. The first side comprises a mold core for forming the thread. The method also involves injecting a liquid polymer into the mold, and allowing the polymer to cool so as to form the cap. After forming the cap, the method further involves separating the first and second sides of the mold without rotating the first side.

These and other aspects of the present application will be apparent from the detailed description below. In no event, however, should the above summaries be construed as limitations on the claimed subject matter, which subject matter is defined solely by the attached claims.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DESCRIPTION OF ILLUSTRATIVE EMBODIMENTS

Embodiments of the present disclosure are directed to disinfecting caps for use with open female luer devices. A luer is a standardized system of fluid fittings, ports, and interfaces that can be used to make fluid-tight connections between medical implements. Luers can include stopcocks and dialysis catheters. Disinfecting caps of the present disclosure are configured to disinfect the face and periphery of an OFL device while providing an airtight and liquid tight seal with the inside lumen of the OFL device. A disinfecting cap of the present disclosure includes features which allow it to work across a wide range of thread variance on different OFL devices, such as stopcocks and dialysis catheters.

Embodiments of the disclosure address the need for a low cost device that can protect, disinfect, and seal OFL devices with significant thread variability due to the large number of manufacturers of these devices. Although there is an ISO (International Standards Organization) standard for threads on female luer lock devices, for example, there is variability in threads between manufacturers which can affect cap functionality. Disinfecting caps of the present disclosure accommodate a wide range of OFL device thread variations and can be molded with a simple nonrotating open and close mold.

Exemplary embodiments provided below are directed to a two-part disinfecting cap arrangement which includes a cap and a movable piston. The cap and movable piston cooperate to actively disinfect exterior surfaces of an OFL device while providing an airtight and liquid-tight seal that holds a predetermined pressure when the cap is rotatably secured to the OFL device. Some embodiments are directed to a cap and a method of making the cap that provide for a thread having a varying height, which may include or exclude a moveable piston.

Figure 1A:
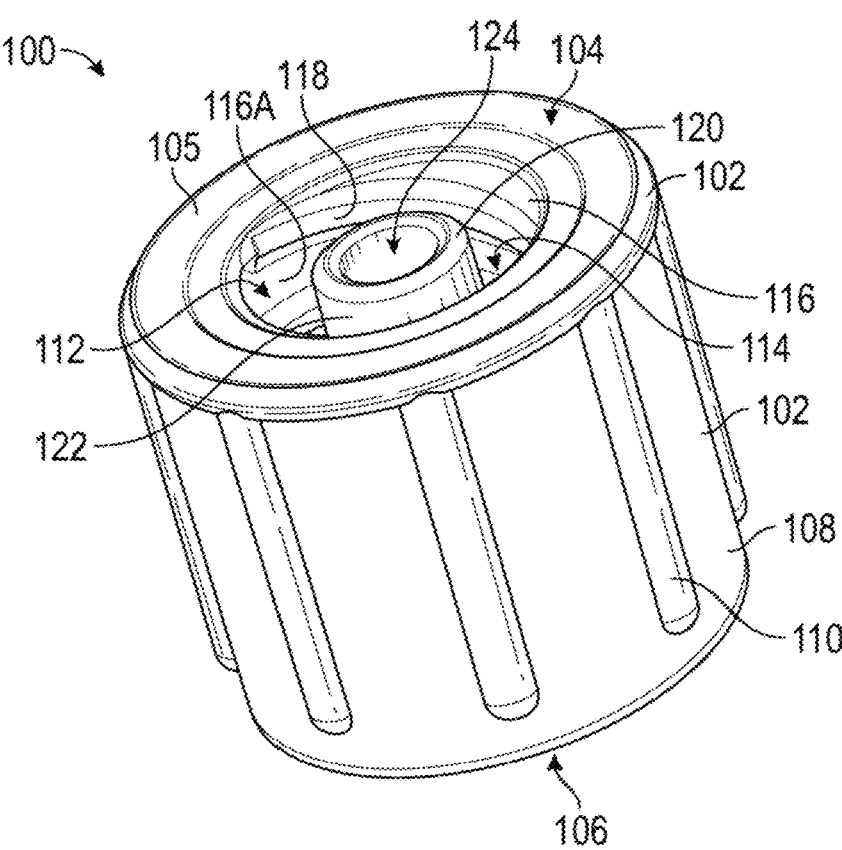
FIG. 1A is a top perspective view of a disinfecting cap configured for use with an OFL device in accordance with various embodiments.
Figure 1B:
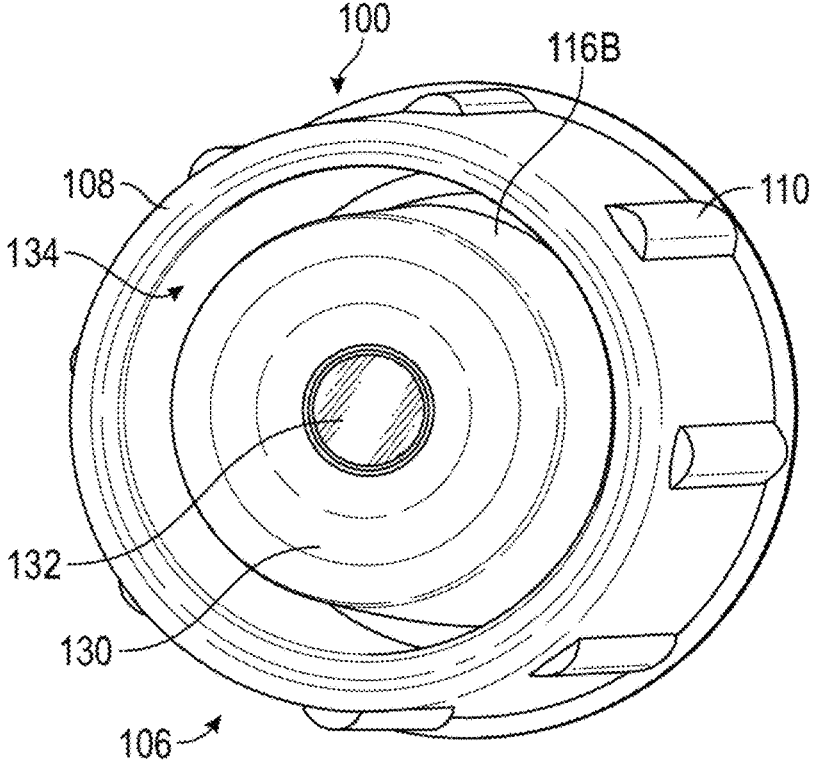
FIG. 1B is a bottom perspective view of the disinfecting cap shown in FIG. 1A.

FIGS. 1A and 1B are perspective views of a disinfecting cap 100 configured for use with an OFL device in accordance with various embodiments. The cap 100 shown in FIG. 1A includes a body 102 comprising a top 104, an opposing bottom 106, a chamber 114 defined between the top 104 and the bottom 106, and an exterior wall 108. The top 104 includes an opening 112 of the chamber 114. The chamber 114 is configured to hold a liquid disinfectant. The liquid disinfectant can be any substance or material that cleans the luer of bacterial and/or viral microorganisms and includes alcohols (e.g., isopropyl alcohol and ethanol), alcohols at various concentrations (e.g. 70%/30% V/V isopropyl alcohol/water), ethanol (ethyl alcohol), chlorhexidine (chlorhexidine gluconate, chlorhexidine acetate), povidone-iodine, hydrogen peroxide, soap, hydrochloric acid, chloroxylenol (PMCX), PHMB (polyhexamethylene biguanide), octenidene, benzalkonium chloride, and combinations thereof.

The top 104 includes a sealing surface 105 to which a removable protective seal (e.g., a foil seal) can be attached to maintain sterility of the chamber 114 prior to use of the cap 100. The exterior wall 108 optionally includes a number of gripping features 110 that are spaced around the periphery of the exterior wall 108. The gripping features 110 facilitate manual manipulation of the cap 100 during use.

The cap body 102 includes a male post 120 situated in chamber 114 which extends from the bottom 106 to approximately the top 104 of the cap body 102. For example, the male post 120 can extend to the top 104 or be recessed from the top 104. In some embodiments, the male post 120 is flush with the top 104 of the cap body 102. In other embodiments, the male post extends to a height below the top 104 of the cap body 102. In FIG. 1A, the male post 120 includes an aperture 124 proximate the opening 112 of the top 104, and is hollow along the axial length of the male post 120. The male post 120 includes a tapered sealing surface 122 which is configured to sealingly contact a tapered inner surface of an OFL device when the cap 100 is fully attached to the OFL device. The taper of the sealing surface 122 of the male post 120 preferably conforms to a known industry standard, such as ISO 594-2 (e.g., a 6% luer taper).

The chamber 114 includes a wall 116 that extends from the top 104 of the cap body 102 to the bottom of the chamber 114 proximate the bottom 106 of the cap body 102. The chamber wall 116 includes an inner surface 116a and an outer surface 116b. The inner surface 116a of the chamber wall 116 includes a thread 118 which originates at or near the opening 112 and extends along the inner chamber wall surface 116a in a spiral configuration. The thread 118 extends from the opening 112 to a predetermined depth into the chamber 114. For example, the thread 118 can extend past the midway point of the chamber 114 but terminate prior to reaching the bottom of the chamber 114. For example, the upper 60% of the inner chamber wall surface 116a can include the thread 118, while the lower 40% of the inner chamber wall surface 116a can be devoid of the thread 118. It is understood that the penetration depth of the thread 118 into the chamber 114 can vary depending on the particular design of the cap 100.

The configuration of the thread 118 can vary. For example, the thread 118 can be a single thread or a double start thread (e.g., a double start, right hand thread). The thread 118 can be a continuous thread or a discontinuous thread. As will be described in greater detail hereinbelow, the thread 118 has a variable thread height. More particularly, the thread 118 has a height that increases as a function of increasing distance from the opening 112 of the chamber 114. This variation in height of the thread 118 advantageously allows the cap 100 to be used across a wide range of thread variance on different OFL devices.

The portion of an OFL device that interacts with the thread 118 can vary significantly across different OFL device designs and manufacturers. For example, the portion of the OFL device that interacts with the thread 118 is commonly referred to as a lug (truncated thread). This portion of the OFL device that interacts with the thread 118 may also be a thread. Alternatively, the portion of the OFL device that interacts with the thread 118 may be a flange with recessed thread, also referred to a negative thread. The choice of the use of a lug, a thread, or a flange with a recessed thread depends upon on the particular design of the OFL. Some OFL devices include lugs disposed on a flange of the OFL device. Other OFL devices are devoid of a flange, and include lugs that extend from the sidewall of the OFL device. In some OFL devices, the flange serves as the lugs. The flange can be continuous (e.g., extending 360° around the OFL device) or discontinuous. For example, a first flange or lug section can be situated on a first surface of the OFL device, and a second flange or lug section can be situated on a second surface spaced from the first surface by 180°.

Although the dimensions of the flange and/or lugs of an OFL device typically conform to an industry standard (e.g., ISO 594-2), these components of the OFL device can vary somewhat from specified dimensions. For example, the width or diameter of the flange and/or lug region of the OFL device can vary from specified dimensions. The variation in height of the thread 118 of the cap 100 advantageously accommodates the different types of OFL device lugs, as well as the dimensional variations of these components. For example, the portion of the thread 118 at or near the opening 112 of the cap body 102 has a relatively low thread height, but is high enough to serve as a thread start for the OFL device. This allows for proper axial orienting of the cap body 102 on the OFL device prior to applying increased torque needed to activate the disinfecting features of the cap 100. As the cap 100 is screwed further onto the OFL device, the lugs of the OFL device engage a portion of the thread 118 having an increased thread height relative to the initial portion, allowing the cap 100 to be securely attached to the OFL device without stripping the thread 118 or overriding the thread 118. On OFL devices with very short lugs, these devices can override and possibly breach the internal male luer post seal that was made without using thread forms of increased height from those at the opening 112.

FIG. 1B is a perspective view of the bottom of the cap 100 shown in FIG. 1A. FIG. 1B shows various features of the bottom 106 of the cap 100. In particular, FIG. 1B shows the bottom 130 of the chamber 114. The center of the chamber bottom 130 defines the base 132 of the upward projecting male post 120. FIG. 1B shows an annular gap 134 defined between the outer surface 116$b$ of the chamber wall 116 and the exterior wall 108 of the cap body 102. The annular gap 134 extends from the bottom 106 of the cap body 102 to a location proximate the top 104. In this configuration, the chamber 114 "hangs" from the upper region of the cap body 102.

Figures 2A, 2B:
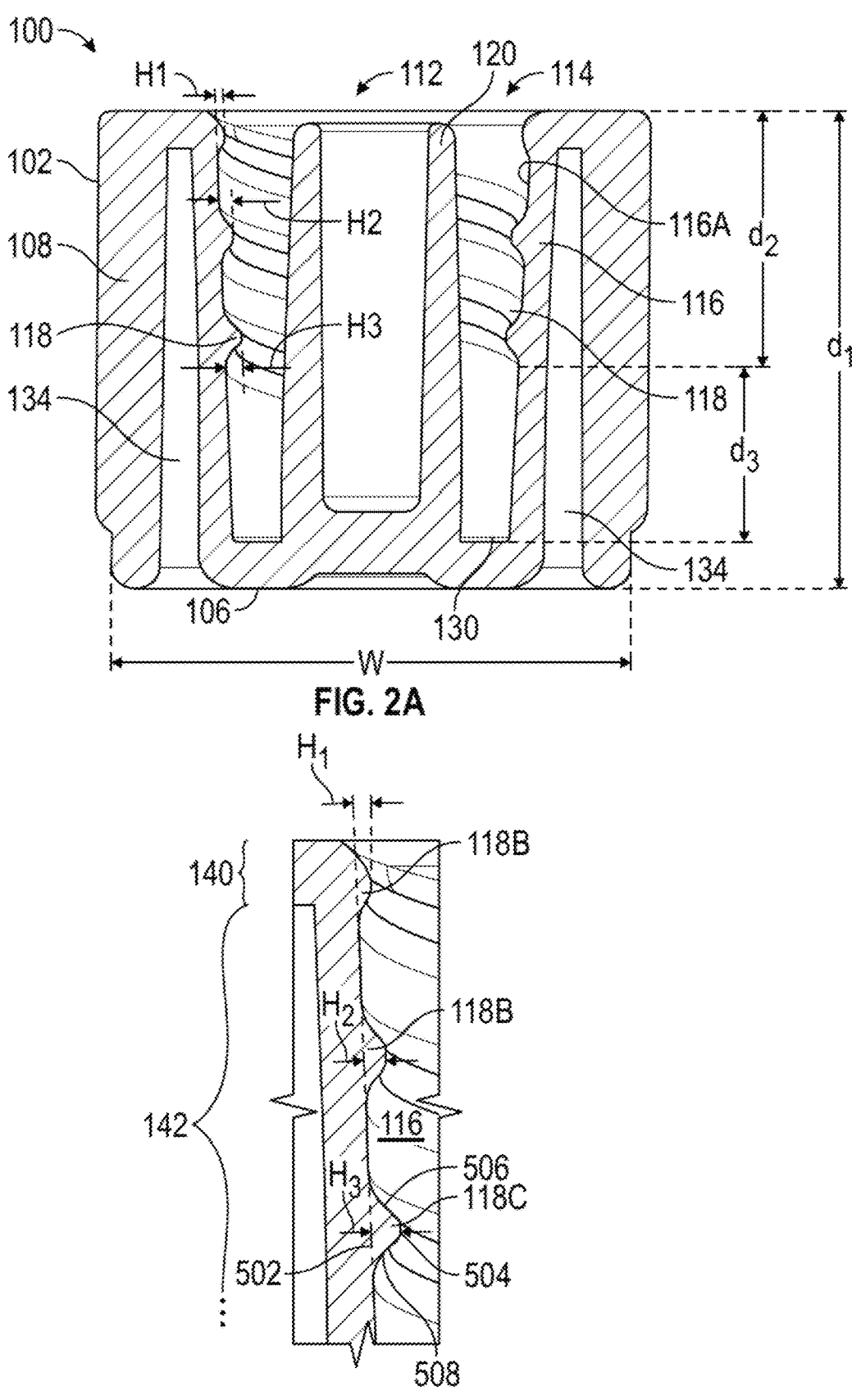
FIG. 2A is a cross-sectional view of the cap shown in FIGS. 1A and 1B.
FIG. 2B shows a thread of the cap illustrated in FIGS. 1A, 1B, and 2A having a variable thread height in accordance with various embodiments.

As is shown in FIG. 2B, this upper region is referred to herein as the mold constrained region 140 of the cap body 102. The region below the mold constrained region 140 (or "constrained region") is referred to herein as the mold unconstrained region 142 (or "unconstrained region") of the cap body 102. As will be discussed in greater detail hereinbelow, the height of the thread 118 within the constrained region 140 is lower than the height of the thread 118 within the unconstrained region 142 of the cap body 102. Because the constrained region 140 of the cap body 102 has little "give" to it (is relatively inflexible) when demolded, the lower profile of the thread 118 within the constrained region 140 allows for demolding of the cap 100 without damaging the thread 118 within the constrained region 140. Also, the annular gap 134 is configured to accommodate lateral flexing or expansion of the chamber wall 116 in the unconstrained region 142 when the cap 100 is demolded, which allows the thread 118 to have a greater height in the unconstrained region 142. The annular gap 134 also allows for flexing or expansion of the chamber wall 116 to accommodate variations in the diameter or width of the lugs of an OFL device. For example, an OFL device may have a flange that is wider than a specified width, which can be accommodated by bowing of the chamber wall 116 due to the presence of the annular gap 134.

According to some embodiments, the cap body 102 need not include the annular gap 134. In such embodiments, the chamber wall 116 is formed from a resilient material, such as a resilient thermoplastic material. The resilient material provides for lateral flexing or expansion of the chamber wall 116 during the demolding process. The resilient material also provides for flexing or expansion of the chamber wall 116 in response to forces generated by the flange or lugs of the OFL device when screwing the cap 100 onto the OFL device. A representative resilient material is one that allows the chamber wall 116 to deflect resiliently without permanent deformation. It is noted that the resiliency of the chamber wall 116 is influenced by the type of material used to form the chamber wall 116 and the thickness of the chamber wall 116.

The flexibility or resiliency of a molded thermoplastic material used to form the chamber wall 116 can be adjusted by the selection of the particular thermoplastic elastomer starting material, and additives, such as, for example a plasticizer(s), which typically are added to make the molded thermoplastic material more flexible. A person of ordinary skill in the art would select the appropriate starting materials and additives to form a molded thermoplastic material with the desired flexibility. As used herein and in the claims, the term "thermoplastic material" means a plastic material that has a softening or melting point, and is substantially free of a three-dimensional crosslinked network resulting from the formation of covalent bonds between chemically reactive groups, e.g., active hydrogen groups and free isocyanate groups. Examples of thermoplastic materials include, but are not limited to, thermoplastic polyurea, thermoplastic polyimide, thermoplastic polyamide, thermoplastic polyamideimide, thermoplastic polyester, thermoplastic polycarbonate, thermoplastic polysulfone, thermoplastic polyketone, thermoplastic polyethylene, thermoplastic polypropylene, thermoplastic polybutylene terephthalate, thermoplastic polyvinylchloride, thermoplastic acrylonitrile-butadiene-styrene, thermoplastic polyurethane and mixtures or thermoplastic compositions containing one or more thereof.

FIG. 2A is a cross-sectional view of the cap 100 shown in FIGS. 1A and 1B. FIG. 2A shows a thread 118 extending along a portion of the inner chamber wall surface 116$a$ in a spiral configuration. As can be seen in the embodiment shown in FIG. 2A, the thread 118 extends from the opening 112 of the cap body 102 and terminates between the opening 112 and the bottom 130 of the chamber 114. For example, and in accordance with some embodiments, the cap body 102 can have a width, w, of 0.540 inches and a height, $d_1$, of 0.467 inches. The chamber 114 can have a depth $(d_2+d_3)$ of 0.422 inches defined between the opening 112 and the bottom 130. The thread 118 can extend from proximate the opening 112 to a depth $d_2$ of 0.254 inches along the inner chamber wall surface 116$a$. The remaining portion of the inner chamber wall surface 116$a$ from the termination of the thread 118 to the bottom 130 of the chamber 114 ($d_3$=0.168 inches) is a smooth surface devoid of the thread 118.

The thread 118 can include a multiplicity of thread portions that progressively increase in terms of thread height as a function of increasing distance from the opening 112. For example, and with reference to FIG. 2B, the thread 118 shown in FIG. 2A can include a first portion 118A proximate the opening 112 having a first thread height, $H_1$, and a second portion 118B spaced apart from the opening 112 by the first thread portion 118A having a second thread height, $H_2$. As can be seen in FIG. 2B, the height, $H_2$, of the second thread portion 118B is greater than the height, $H_1$, of the first thread portion 118A. It is noted that thread height refers to the dimension of the thread 118 that is perpendicular to the inner chamber wall surface 116$a$. Subsequent thread portions can be the same height or higher than the second thread portion 118B.

For example, in some embodiments, the thread 118 can include a first portion 118A having a thread height of $H_1$, a second portion 118B having a thread height of $H_2$, and a third portion 118C having a thread height of $H_3$. In this illustrative example, the thread height of thread portions 118A, 118B, and 118C increases as a function of increasing distance from the opening 112, such that $H_3>H_2>H_1$. In some embodiments, the thread height of thread portions 118A, 118B, and 118C increases as a function of increasing distance from the opening 112, such that $H_3 \geq H_2>H_1$. The transition from one thread height to another can be gradual or abrupt.

In general, the portion or portions of the thread 118 in the constrained region 140 of the cap body 102 have a thread height lower than that of the portion or portions of the thread 118 in the unconstrained region 142 of the cap body 102. It is understood that the thread 118 includes at least two thread portions having different thread heights, such that the thread portion nearest the opening 112 has a thread height lower than the thread portion further from the opening 112. It is also understood that the thread 118 may include more than two thread portions (e.g., 3 or 4 thread portions) each having a different thread height.

According to some embodiments, and with continued reference to FIG. 2B, the first thread height, $H_1$, of the first thread portion 118A can be about half the thread height, $H_2$, of the second thread portion 118B. In other words, the thread height $H_2$ can be at least about 100% higher than the thread height $H_1$. The second thread portion 118B can have a thread height $H_2$ that is at least 50%, 100%, or 150% greater than the thread height, $H_1$, of the first thread portion 118A. For example, the first thread height, $H_1$, can be 0.008 inches, and the second thread height, $H_2$, can be 0.015 inches. In the illustrative example shown in FIG. 2B, the third thread height, $H_3$, is greater than 0.015 inches (e.g., 0.020 inches), but may alternatively be the same as $H_2$ (e.g., 0.015 inches).

As is further shown in FIG. 2B, the thread 118 has a threadform or shape that is relatively rounded, which is in contrast to a conventional trapezoidal (angular) thread. For example, the thread portion 118C shown in FIG. 2B includes a root 502, a crest 504, and tapered or radiused surfaces 506 and 508. The radiused surfaces 506 and 508 of the thread 118 facilitate demolding of the 100 without damaging the thread 118 when using a non-rotating open and close mold. In some embodiments, the thread 118 can have an angular threadform (e.g., trapezoidal) or other shape. Although radiused surfaces are shown for purposes of illustration, other shapes are contemplated. For example, angular threadforms can be employed when using molds having rotating cores.

The cap body 102 can be formed from a thermoplastic material. For example, the cap body 102 can be formed from high-density polyethylene (HDPE) or from any of the thermoplastic materials listed hereinabove.

Figure 5A:
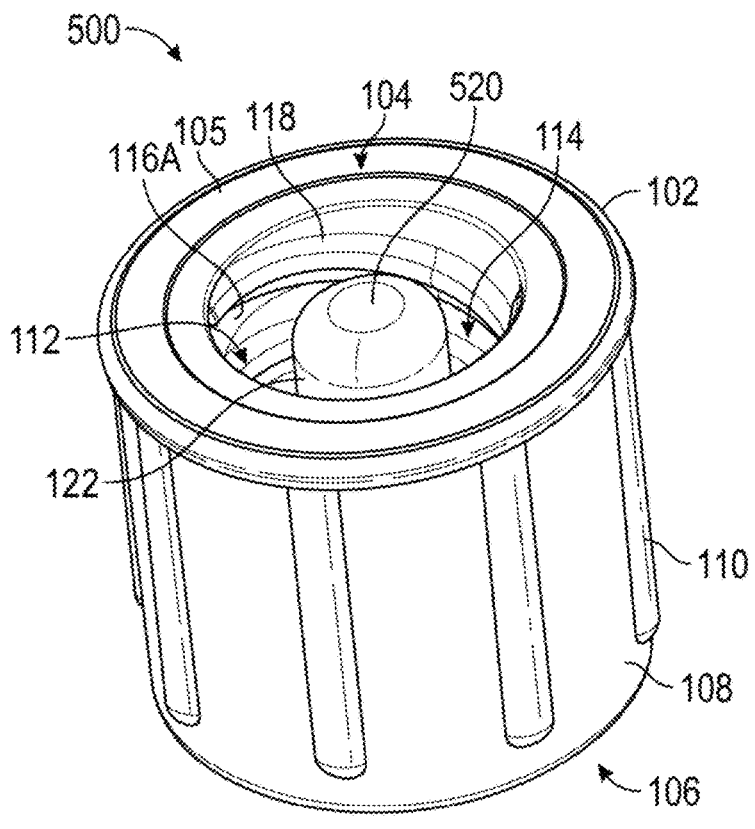
FIG. 5A is a top perspective view of an alternative disinfecting cap configured for use with an OFL device in accordance with various embodiments.
Figure 5B:
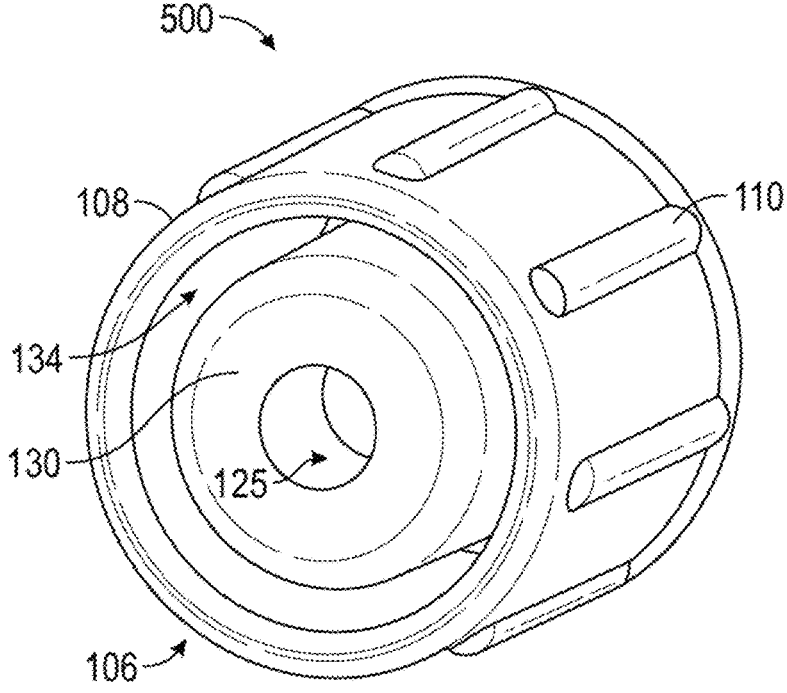
FIG. 5B is a bottom perspective view of the disinfecting cap shown in FIG. 5A.

FIGS. 5A and 5B are perspective views of a disinfecting cap 500 configured for use with an OFL device in accordance with other embodiments. The cap 500 shown in FIGS. 5A and 5B is largely the same as the cap 100 shown in FIGS. 1A and 1B. As such, the description of features common to caps 100 and 500 is not repeated in this discussion. The cap 500 differs from the cap 100 in terms of the male post feature. More particularly, the male post 520 shown in FIG. 5A has a solid top surface (terminal end surface), whereas the top surface of the male post 120 shown in FIG. 1A has an aperture 124. As is shown in FIG. 5B, the bottom 130 of the chamber 114 includes a male post aperture 125, whereas the bottom 130 of the chamber 114 shown in FIG. 1B has a solid base 132 for the male post 120.

Figure 3A:
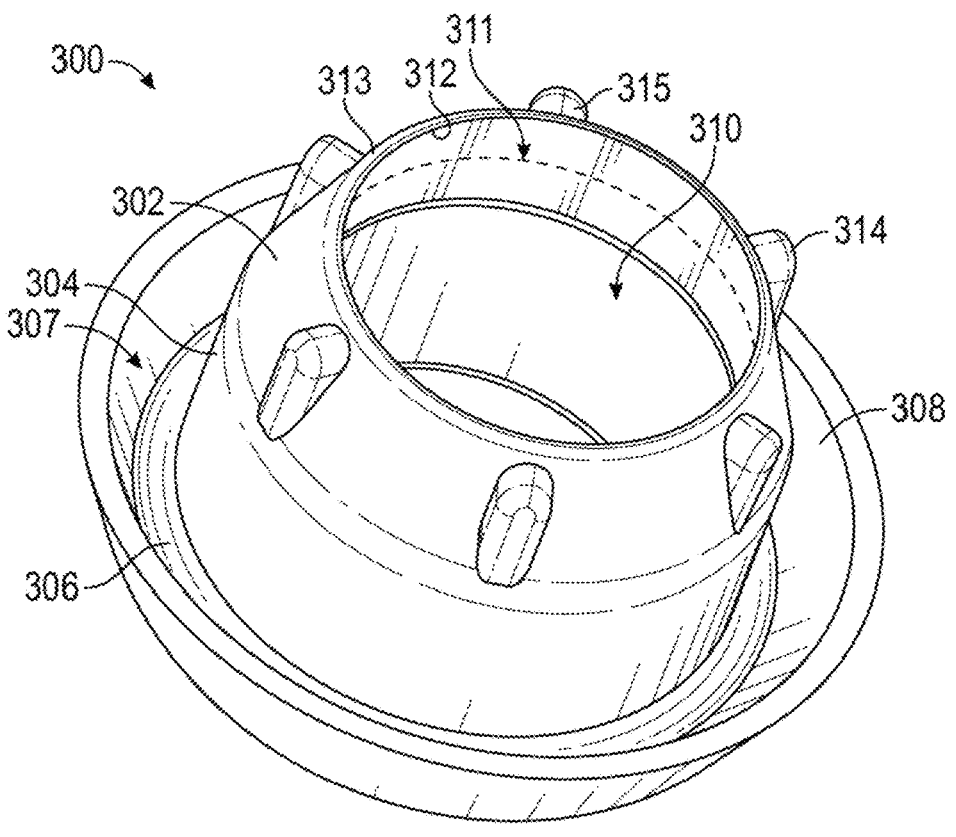
FIG. 3A is a top perspective view of a piston configured to cooperate with the cap shown in FIGS. 1A-1B and 2A-2B to sealingly engage an OFL device in accordance with various embodiments.
Figure 3B:
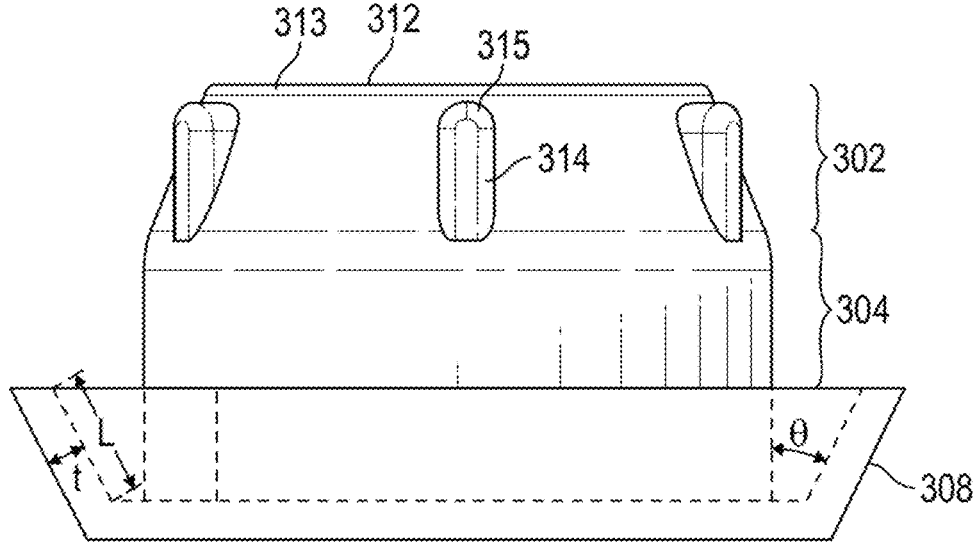
FIG. 3B is a cross-sectional view of the piston shown in FIG. 3A.

FIGS. 3A and 3B show a piston 300 configured to cooperate with the cap 100 shown in FIGS. 1A-1B and 2A-2B to sealingly engage an OFL device in accordance with various embodiments. The piston 300 shown in FIGS. 3A and 3B includes a top region 302, a body region 304, a bottom region 306, and a skirt 308. The piston 300 includes a central opening 310 that extends axially through the piston 300. A sealing surface 312 of the central opening 310 is dimensioned to provide an interference fit with the male post 120 as the piston 300 is moved axially relative to the male post 120.

More particularly, the top region 302 of the piston 300 includes the sealing surface 312 which is dimensioned to provide an interference fit with the male post 120. The sealing surface 312 of the piston 300 is a thin wall structure that can stretch and contract in response to the changing diameter of the tapered sealing surface 122 of the male post 120 as the piston 300 is moved axially relative to the mail post 120. The sealing surface 312 prevents direct injection of the disinfectant up the central opening 310 of the piston 300 and between the piston 300 and the male post 120. The sealing surface 312 of the top region 302 can be limited to the lip region 311 of the piston 300 or can extend axially between the lip region 311 and the body region 304 of the piston 300. The top region 302 also includes a lumen seal 313 defined along the exterior lip region of the piston 300. The lumen seal 313 is configured to sealingly contact an inner wall of an OFL device when the OFL device contacts the piston 300 (see, e.g., FIGS. 4B-4D). The lumen seal 313 provides a seal along the circumference of the OFL device to prevent direct injection of a disinfection solution contained within the chamber 114 into the lumen during the activation cycle of the cap 100.

The top region 302 of the piston 300 also includes a plurality of ribs 314 positioned about a periphery of the top region 302. Each of the ribs 314 has a top surface 315 which is configured to contact a contacting surface of the OFL device when the OFL device is screwed into the opening 112 of the cap body 102. The ribs 314 serve as vertical strengthening members that provide strength in order to prevent the piston 300 from buckling and binding when the OFL device forcibly contacts the piston 300 during the activation cycle. Each of the ribs 314 has a contact surface area where each rib 314 contacts the top region 302. The cumulative contact surface area of all of the ribs 314 is limited to ensure that the top region 302 can stretch and maintain an interfering fit with the male post 120 as the piston 300 moves axially on the male post 120. For example, the cumulative contact surface area for all of the ribs 314 is less than about 50% of a total surface area of the top region 302.

The body region 304 and the bottom region 306 are relatively rigid relative to the top region 302. This can be accomplished, for example, by using different materials to construct these regions 304, 306 or increasing the thickness of the material in these regions 304, 306. The body and bottom regions 304 and 306 provide structural integrity for the piston 300 as these regions preferably do not flex during the activation cycle of the cap 100. Projecting upwardly at an acute angle (θ) from the bottom 306 of the piston 300 is a flexible circumferential skirt 308. The skirt 308 is dimensioned to contact the inner chamber wall surface 116a and to flex in response to changes in the contour of the inner chamber wall surface 116a (e.g., such as due to the presence of the thread 118), to form a temporary seal that inhibits leakage of a liquid disinfectant contained within the chamber 114. In some embodiments, the skirt 308 can have a length, L, (e.g., 0.036 inches) and a thickness, t, (e.g., 0.010 inches), such that the length, L, is greater than the threadform height (H) of the thread 118 (e.g., L>H by at least 2×).

The piston 300 can be formed from a thermoplastic material. For example, the piston can be formed from HDPE or from any of the thermoplastic materials listed hereinabove.

Figure 4A:
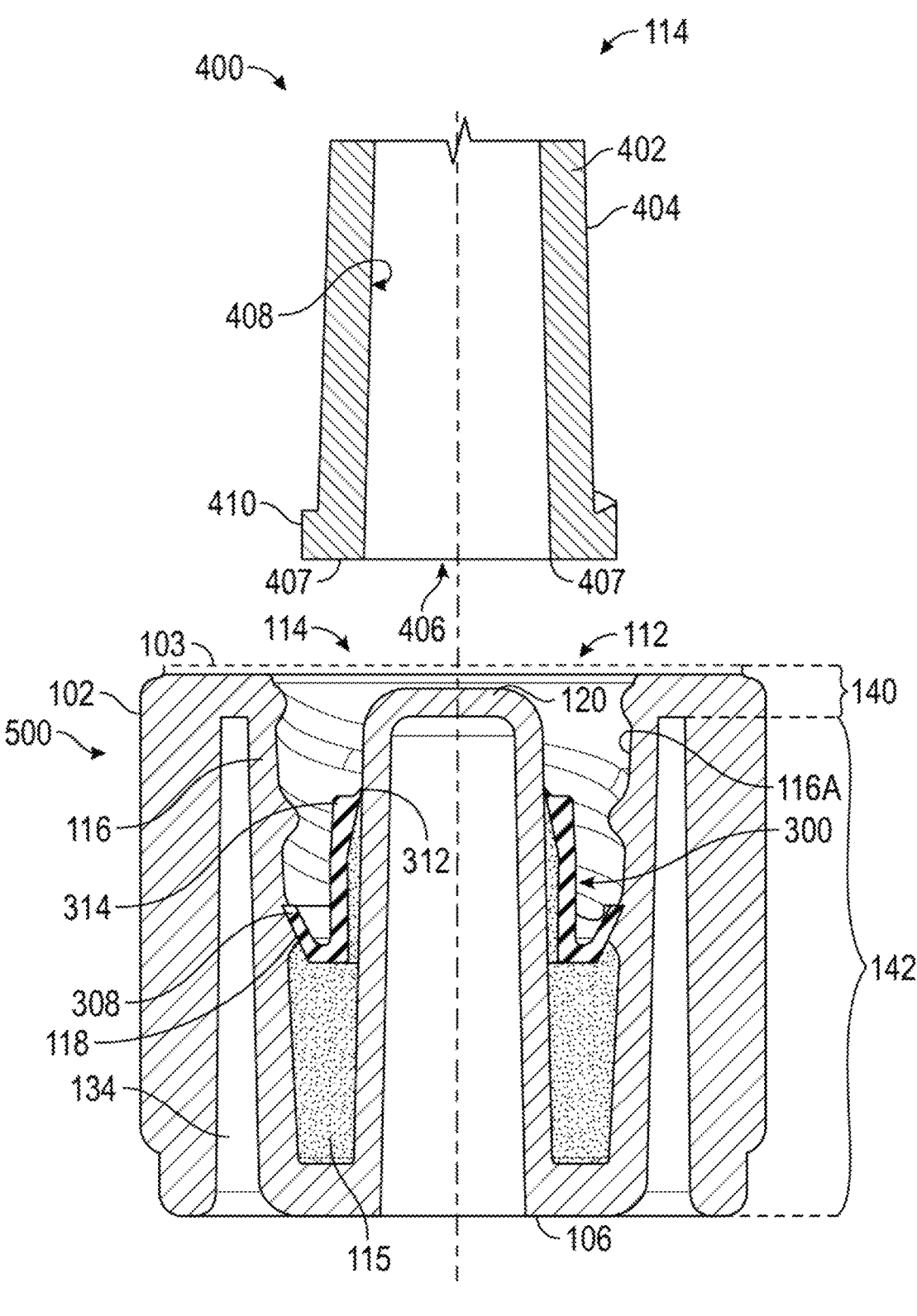
FIG. 4A shows a disinfecting cap in proximity to an OFL device prior to contact between the cap and the OFL device in accordance with various embodiments.
Figure 4B:
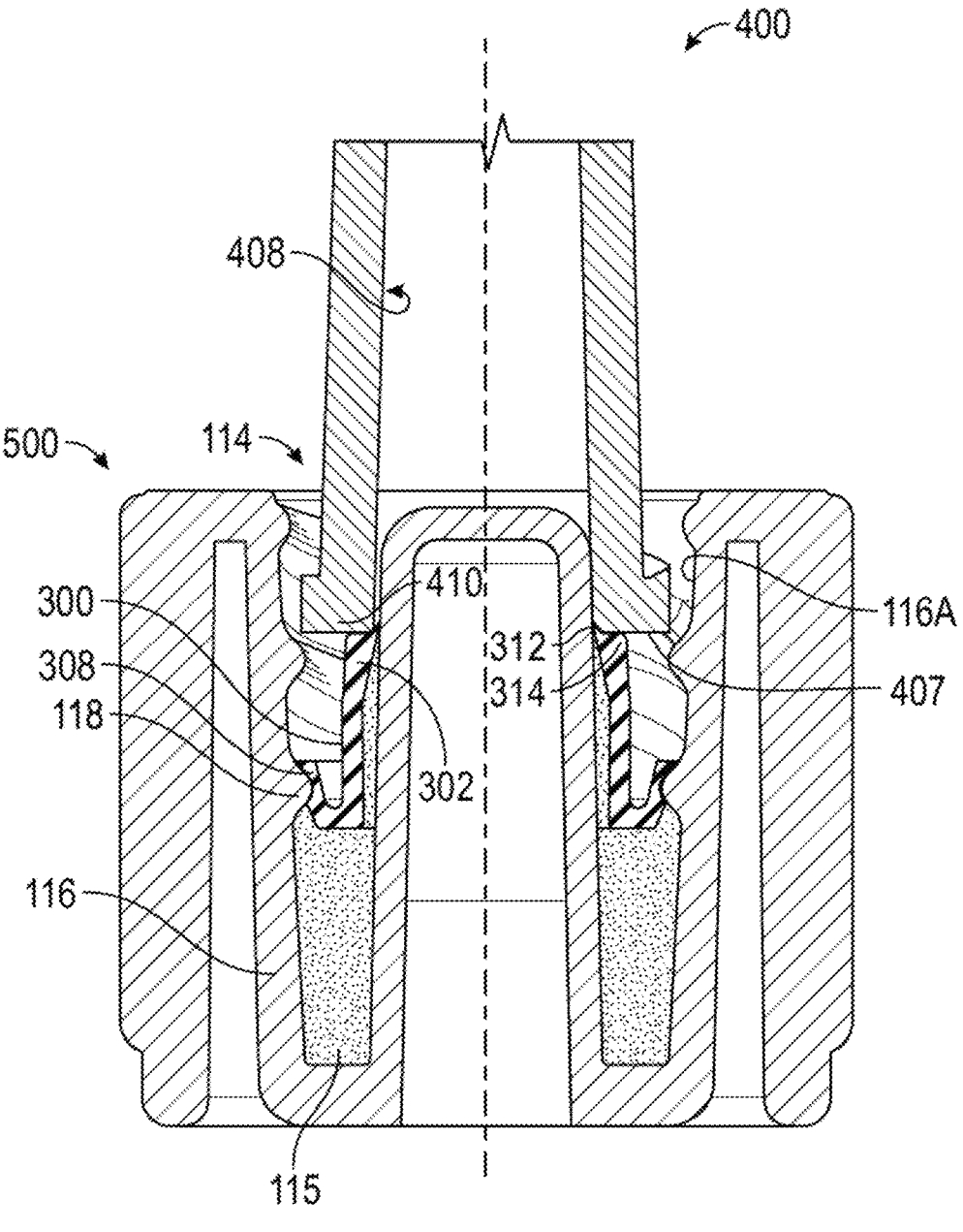
FIG. 4B shows contact between an OFL device and the piston of a disinfecting cap prior to activation of the piston in accordance with various embodiments.
Figures 4C, 4D:
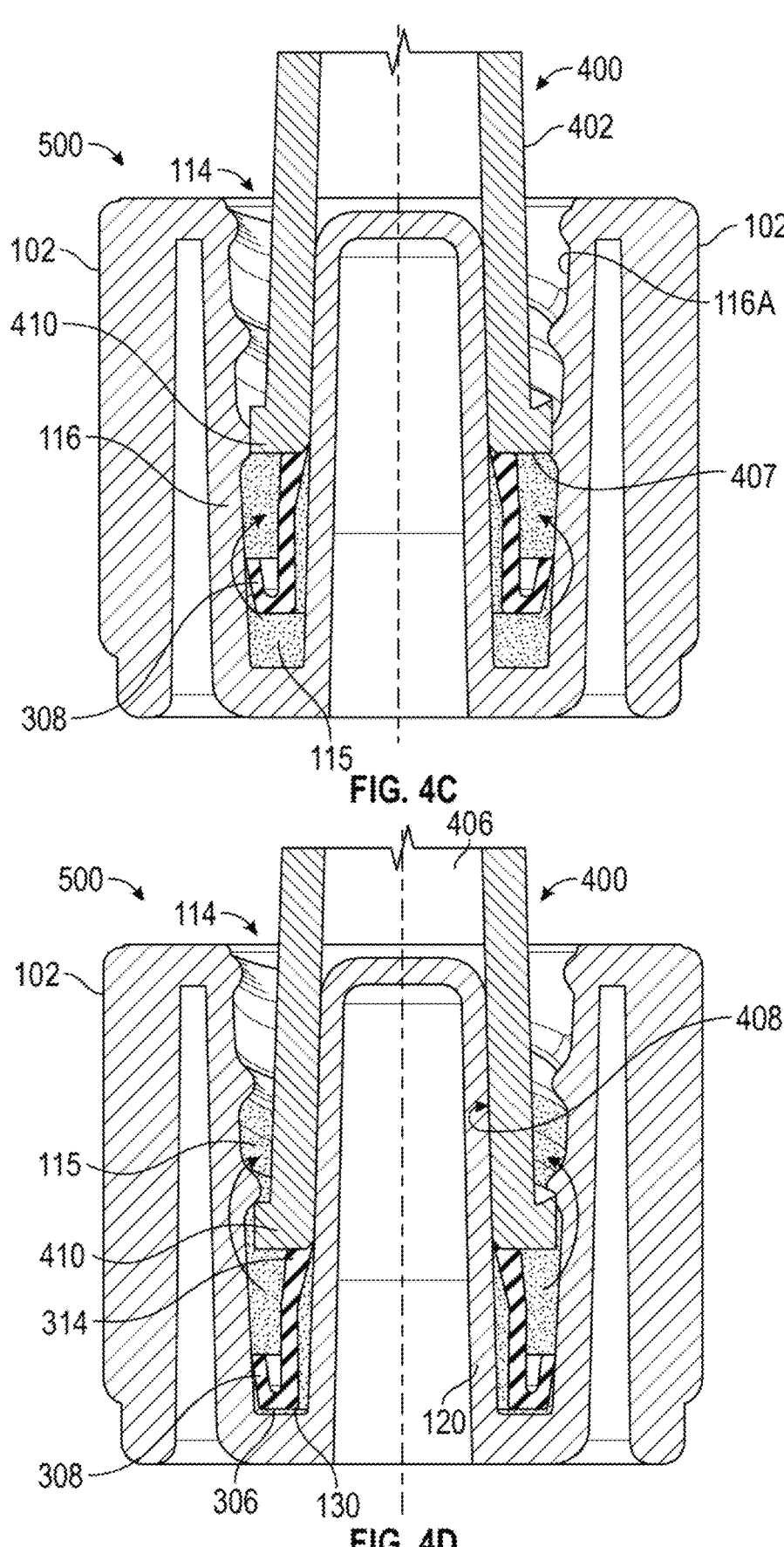
FIG. 4C shows activation of the piston of a disinfecting cap in response to forcible contact between an OFL device and the piston in accordance with various embodiments.
FIG. 4D shows mating contact between the tapered male post of a disinfecting cap and the tapered inner surface of an OFL device after activation of a piston of the cap in accordance with various embodiments.

FIGS. 4A-4D are cross-sectional views showing interaction between the disinfecting cap 500 and an OFL device 400 in accordance with various embodiments. FIG. 4A shows the cap 500 in proximity to the OFL device 400 prior to contact between the cap 500 and the OFL device 400. FIG. 4B shows contact between the OFL device 400 and the piston 300 of the cap 500 prior to activation of the piston 300. In FIGS. 4A and 4B, the piston 300 is shown in its pre-activation state. FIG. 4C shows activation of the piston 300 in response to forcible contact between the OFL device 400 and piston 300. In FIG. 4C, the piston 300 is shown in an activation state. FIG. 4D shows the piston 300 in its post-activation state. FIG. 4D shows mating contact between the tapered male post 120 of the cap 500 and the tapered inner surface of the OFL device 400 after activation of the piston 300.

As is shown in FIG. 4A, the OFL device 400 has a body 402 which includes an exterior surface 404, a lumen 406, and a tapered inner wall 408. The taper of the inner wall 408 corresponds to a taper of the male post 120 (e.g., an ISO specified taper, such as 6%). The distal end of the body 402 includes a contacting surface 407 (e.g., the face of the OFL device 400) which is configured to contact the piston 300 when the cap 500 is screwed onto the OFL device 400. The contacting surface 407 includes a flange 410. The flange 410 is dimensioned to interact with the thread 118 extending along the inner chamber wall surface 116a, allowing the cap body 102 to screw onto the luer body 402. For example, the flange 410 may incorporate a thread(s) or lug(s) dimensioned to receive the thread 118 as the cap body 102 is screwed onto the luer body 402. In some configurations, the luer body 402 includes a continuous circumferential flange 410. In other configurations, the flange 410 may be discontinuous. For example, a first portion of the flange 410 may be positioned at a first position of the luer body 402, while a second portion of the flange 410 may be situated at a second position of the luer body 402, where the first and second positions are separated by 180°.

In the pre-activation state, as is shown in FIG. 4A, a liquid disinfectant 115 is contained within the chamber 114. The disinfectant 115 is prevented from escaping the chamber 114 by an interference fit between the sealing surface 312 of the piston 300 and the tapered surface of the male post 120. The disinfectant 115 is also prevented from escaping the chamber 114 by a temporary seal created between the skirt 308 of the piston 300 and the thread 118 of the inner chamber wall surface 116a. As was discussed previously, the skirt 308 is sufficiently pliable to generally conform to the shape of the rounded thread 118 so as to create a temporary seal between the piston 300 and the inner chamber wall surface 116a. To maintain sterility of the disinfectant cap 500 prior to use, a removable foil seal 103 is attached to the sealing surface 105 of the top 104 of the cap body 102 with, for example, an adhesive or heat seal process. The foil seal 103 is removed from the cap top 102 prior to attaching the cap 500 to the OFL device 400.

FIG. 4B shows the cap 500 partially attached to the OFL device 400. In FIG. 4B, the piston 300 is in a pre-activation state with the contacting surface 407 of the OFL device 400 just making contact with the ribs 314 of the top region 302 of the piston 300. The relatively low height of the thread 118 at and above the position of the flange 410 of the OFL device 400 shown in FIG. 4B is adequate to allow initial threading of the cap body 102 onto the OFL device 400. The initial low height of the thread 118 (e.g., in the constrained region 140) allows threading of the cap 500 onto the OFL device 400 to occur at or near the opening 112. Early threading of the cap 500 onto the OFL device 400 advantageously allows the cap 500 and the piston 300 to be axially aligned with the OFL device 400, and provides for a shorter overall cap height. The flange 410 of the OFL device 400 is shown engaging the thread 118 of the inner chamber wall surface 116a as the cap 500 is screwed onto the OFL device 400. With the piston 300 in its pre-activation state, the skirt 308 forms a temporary seal with the thread 118 to inhibit leakage of the liquid disinfectant 115 from the chamber 114. Also, the interference fit between the sealing surface 312 of the piston 300 and the tapered surface of the male post 120 prevents the disinfectant 115 from escaping the chamber 114.

FIG. 4C shows the piston 300 of the cap 500 in an activation state, with force being applied to the piston 300 by the OFL device 400 as the cap 500 is screwed onto the OFL device 400. As the cap 500 is screwed onto the OFL device 400 during the activation state, the contacting surface 407 of the luer body 402 forces the piston 300 to move axially over the male post 120 deeper into the chamber 114. The downward movement of the piston 300 into the chamber 114 causes the liquid disinfectant 115 to flow between the pliable skirt 308 and the inner chamber wall surface 116a. The liquid disinfectant 115 that escapes from the chamber 114 flows over exterior surfaces of the OFL device 400 encompassed by the cap body 102, thereby disinfecting these surfaces of the OFL device 400. As was discussed previously, the lumen seal 313 of the piston 300 forms a liquid tight seal with the interior circumferential surface of the OFL device 400 at the contacting surface 407 which prevents the liquid disinfectant 115 from entering the lumen 406 of the OFL device 400.

FIG. 4D shows the piston 300 of the cap 500 in a post-activation state, where the exterior surfaces of the OFL device 400 have been disinfected. Although the piston 300 is shown resting on the bottom 130 of the chamber 114 in FIG. 4D, it should be understood that the final location of the piston 300 may vary with OFL device. In the post-activation state, the male post 120 of the cap body 102 forms an airtight and liquid-tight seal with the inner wall 408 of the OFL device 400 that can handle a predetermined pressure, such as that specified in ISO 594-2. The lumen seal 313 of the piston 300 continues to provide a liquid tight seal with the interior circumference surface of the OFL device 400 at the contacting surface 407. It is noted that the higher height of the thread 118 provided for cap activation allows OFL devices with short lugs or threads to make proper attachment with the cap body 102 without stripping the thread 118, and allows the male post 120 to securely form a mating seal with the inner wall 408 of the OFL device 400. Also, the compliance of the chamber wall 116 allows for variance in the diameter or width of the lug/thread of the OFL device 400 while still allowing adequate travel for the male post 120 to securely form a mating seal with the inner wall 408 of the OFL device 400. When access to the lumen 406 of the OFL device 400 is desired, the cap 500 is unscrewed from the OFL device 400.

Figure 6:
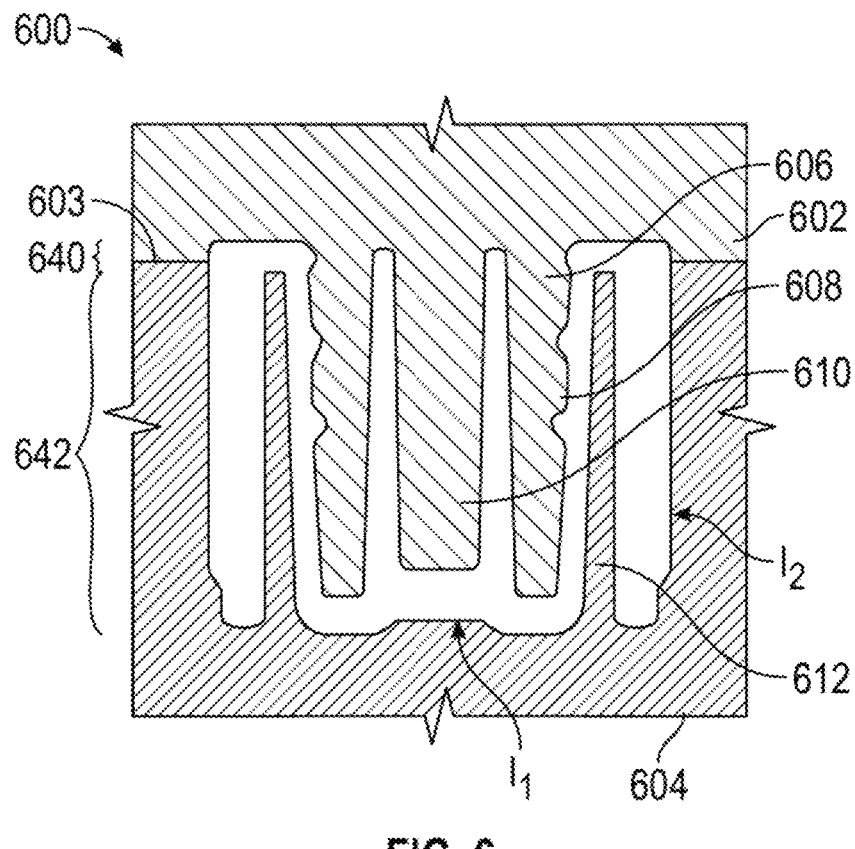
FIG. 6 is a cross-sectional view of an open and close mold that can be used to form a disinfectant cap comprising a thread having a variable thread height in accordance with various embodiments.

FIG. 6 shows an open and close mold 600 that can be used to form a disinfecting cap such as those discussed hereinabove in accordance with various embodiments. In some embodiments, the mold 600 purposefully lacks rotating cores for forming thread features of the cap. Using an open and close molding strategy that lacks rotating cores for forming thread features introduces challenges to the thread design due to the severe undercuts in the molding process by the thread features. Conventional techniques for molding threaded caps require the use of rotating cores in order to create the threads and to prevent damage to the threads during the demolding process. Various embodiments of the disclosure provide a disinfecting cap having a thread design that improves functionality while also addressing the issue of being able to be manufactured with a non-rotating open and closed mold and using semi-rigid materials. Some embodiments provide a disinfecting cap having a thread that varies in height which can be manufactured using a mold comprising rotating cores and using semi-rigid or resilient materials.

The representative mold shown in FIG. 6 is configured to form the cap 100 shown in FIGS. 1A and 1B. The mold 600 includes a first side 602 and a second side 604. The first side 602 includes a feature 606 that forms the chamber 114 shown in the previous figures. In particular, the feature 606 includes a mold core 608 that forms the thread 118 having a variable thread height. The first side 602 includes a feature 610 that forms the male post 120. The second side 604 includes a feature 612 that forms the annular gap 134 shown in the previous figures. When forming the cap 100 shown in FIGS. 1A and 1B (male post 120 with an aperture 124), polymeric material can be injected from the bottom of the mold at a location $I_1$. Injecting the polymeric material from the bottom of the mold provides for a uniform material flow while filing the mold 600 and improves the moldability of the cap 100. When forming the cap 500 shown in FIGS. 5A and 5B (male post 520 with solid top surface and bottom aperture 125), polymeric material can be injected from the side of the mold at a location $I_2$, since the bottom 130 of the chamber 114 includes the aperture 125 at the base of the male post 520.

During molding and demolding operations, the first and second side 602 and 604 move axially relative to one another. Notably, the first side 602 does not include a rotating core (e.g., a rotating mold core 608) for forming the spiral thread 118 of the inner chamber wall surface 116a. Instead of using a rotating core, the mold 600 exploits the variable thread height feature previously discussed to prevent damage to the thread 118 during the demolding process. In particular, the thread 118 in the constrained region 640 of the mold 600 is lower than the height of the thread 118 in the unconstrained region 642 of the mold 600. During demolding, the annular gap 134 created by the mold feature 612 accommodates flexing of the chamber wall 116 in the unconstrained region 642 to avoid damage to the thread 118 in the unconstrained region 642.

The mold 600 shown in FIG. 6 can be used or modified to form the cap 100/500 shown in the previous figures. According to some embodiments, a method of molding the cap 100/500 involves providing a mold 600 comprising at least a first side 602 and a second side 604. The first side 602 is shown to be separated from the second side 604 by the mold parting line 603. The first side 602 comprises a thread groove 608 for forming a thread 118 having a variable thread height. The method involves injecting a liquid polymer into the mold, and allowing the polymer to cool so as to form the cap 100/500. After forming the cap, the method further involves separating the first and second sides of the mold without rotating the first side 602. In other embodiments, the first side 602 can include a rotating core for forming the spiral thread 118, and the rotating core would rotate when separating the first and second sides 602 and 604 during demolding.

This Disclosure Includes the Following Items

Item 1. A cap configured for removable attachment to an open female luer device, the open female luer device having an open distal end with a contacting surface, and the cap comprising:
a body comprising an opening configured to receive the female luer device, a bottom, and a chamber defined between the opening and the bottom, the chamber configured to hold a liquid disinfectant;
a male post in the chamber and dimensioned to receive the female luer device, the male post projecting from the bottom towards the opening of the body and comprising a taper corresponding to a taper of the female luer device;

a wall of the chamber comprising a thread originating proximate the opening and extending into the chamber, a least a portion of the thread having a height that increases as a function of increasing distance from the opening; and
a movable piston positioned about the male post, the movable piston comprising:
a central opening dimensioned to provide an interference fit with the male post;
a top region comprising a sealing surface configured to form a seal with an inner surface of the open distal end of the female luer device; and
a flexible circumferential skirt dimensioned to contact the wall of the chamber.

Item 2. The cap according to item 1, comprising a plurality of ribs positioned about a periphery of the top region.

Item 3. The cap according to any one of the preceding items, wherein:
each of the ribs has a contact surface area where each rib contacts the top region of the movable piston; and
a cumulative contact surface area for all of the ribs is less than about 50% of a total surface area of the top region.

Item 4. The cap according to any one of the preceding items, wherein:
the body comprises a constrained region proximate the opening and an unconstrained region; and
the thread in the constrained region has a height lower than a height of the thread in the unconstrained region.

Item 5. The cap according to item 4, wherein the height of the thread in the unconstrained region increases as a function of increasing distance from the constrained region.

Item 6. The cap according to any one of the preceding items, wherein:
the thread comprise a first portion and a second portion;
the first portion is closer to the opening than the second portion; and
the second portion has a height that is at least about 50% to 150% higher than the first portion.

Item 7. The cap according to any one of the preceding items, wherein the thread has a radiused surface.

Item 8. The cap according to any one of the preceding items, wherein:
the body comprises an exterior wall; and
an annular gap is defined between the chamber and the exterior wall, the annular gap extending axially between the opening and the bottom.

Item 9. The cap according to item 8, wherein the annular gap is configured to accommodate flexing of the chamber.

Item 10. The cap according to any one of the preceding items, wherein the chamber wall is resilient.

Item 11. The cap according to any one of the preceding items, wherein the skirt has a length that is greater than the height of the thread.

Item 12. The cap according to any one of the preceding items, wherein a terminal end surface of the male post facing the opening is solid.

Item 13. The cap according to any one of items 1-11, wherein:
a terminal end surface of the male post facing the opening has an aperture; and
at least a portion of the male post is hollow.

Item 14. The cap according to any one of the preceding items, wherein the cap is formed from a thermoplastic material.

Item 15. The cap according to any one of the preceding items, wherein the cap is formed from high-density polyethylene (HDPE). Item 16. The cap according to any one of the preceding items, comprising a removable foil seal covering the opening.

Item 17. The cap according to any one of the preceding items, comprising a disinfectant.

Item 18. A cap, comprising:

a body comprising an opening, a bottom, and a chamber defined between the opening and the bottom, the chamber configured to hold a liquid disinfectant;

a male post extending from the bottom towards the opening of the body; and a wall of the chamber comprising a thread originating proximate the opening and extending into the chamber, at least a portion of the thread having a height that increases as a function of increasing distance from the opening.

Item 19. The cap according to item 18, wherein the male post has a predefined taper.

Item 20. The cap according to item 18 or item 19, wherein:

the body comprises a constrained region proximate the opening and an unconstrained region; and the thread in the constrained region has a height lower than a height of the thread in the unconstrained region.

Item 21. The cap according to any one of items 18-20, wherein the thread has a radiused surface.

Item 22. The cap according to any one of items 18-21, wherein:

the body comprises an exterior wall; and an annular gap is defined between the chamber and the exterior wall, the annular gap extending axially between the opening and the bottom.

Item 23. The cap according to any one of items 18-22, wherein the chamber wall is resilient.

Item 24. The cap according to any one of items 18-23, wherein a terminal end surface of the male post facing the opening is solid.

Item 25. The cap according to any one of items 18-23, wherein:

a terminal end surface of the male post facing the opening has an aperture; and at least a portion of the male post is hollow.

Item 26. The cap according to any one of items 18-25, comprising a movable piston having a central opening dimensioned to provide an interference fit with the male post.

Item 27. The cap according to item 26, wherein a top region of the piston comprises a sealing surface.

Item 28. The cap according to item 26 or item 27, wherein the piston comprises a plurality of ribs positioned about a periphery of a top region of the piston.

Item 29. The cap according to item 28, wherein:

each of the ribs has a contact surface area where each rib contacts the top region; and a cumulative contact surface area for all of the ribs is less than about 50% of a total surface area of the top region.

Item 30. The cap according to any one of items 27-29, wherein the piston comprises a flexible circumferential skirt dimensioned to contact the wall of the chamber.

Item 31. The cap according to any one of items 18-30, wherein the cap is formed from a thermoplastic material.

Item 32. The cap according to any one of items 18-31, wherein the cap is formed from high-density polyethylene (HDPE).

Item 33. The cap according to any one of items 18-32, comprising a removable foil seal covering the opening.

Item 34. The cap according to any one of items 18-33, comprising a disinfectant in the chamber.

Item 35. A method of molding the cap according to item 23, comprising:

providing a mold comprising at least a first side and a second side, the first side comprising a mold core for forming the thread;

injecting a liquid polymer into the mold;

allowing the polymer to cool so as to form the cap; and after forming the cap, separating the first and second sides of the mold without rotating the first side.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Various modifications and alterations of these embodiments will be apparent to those skilled in the art and it should be understood that this scope of this disclosure is not limited to the illustrative embodiments set forth herein. For example, the reader should assume that features of one disclosed embodiment can also be applied to all other disclosed embodiments unless otherwise indicated.

What is claimed is:

1. A method of molding a cap configured for removable attachment to a medical device, the method comprising:

providing a mold comprising at least a first side and a second side, the first side comprising a mold core for forming a thread;

injecting a liquid polymer into the mold;

allowing the polymer to cool so as to form the cap; and after forming the cap, separating the first and second sides of the mold without rotating the first side;

wherein the cap comprises:

a body comprising an opening, a bottom, and a chamber defined between the opening and the bottom;

a wall of the chamber comprising the thread originating proximate the opening and extending into the chamber by a height, wherein the height of the thread increases as a function of increasing distance from the opening;

the method further comprising introducing a liquid disinfectant into the chamber.

2. The method according to claim 1, the cap further comprising a male post in the chamber and projecting from the bottom towards the opening of the body and a movable piston around the male post.

3. The method according to claim 2, wherein the movable piston comprises:

a central opening with an interference fit surrounding the male post;

a top region extending from the central opening and comprising a sealing surface; and a flexible circumferential skirt in slidable contact with the wall of the chamber.

4. The method according to claim 3, wherein the skirt has a length that is greater than the height of the thread.

5. The method according to claim 2, wherein a terminal end surface of the male post facing the opening is solid.

6. The method according to claim 2, wherein:

a terminal end surface of the male post facing the opening has an aperture; and at least a portion of the male post is hollow.

7. The method according to claim 2, wherein the male post comprises a taper with a diameter near the bottom that is larger than a diameter near the opening.

8. The method according to claim 1, wherein:

the body comprises a constrained region where the body of the cap is in direct contact with the wall of the chamber proximate the opening and an unconstrained region where the body of the cap is spaced apart from the wall of the chamber; and the thread in the constrained region has a height lower than a height of the thread in the unconstrained region.

9. The method according to claim 1, wherein:

the thread comprise a first portion and a second portion;

the first portion is closer to the opening than the second portion; and the second portion has a height that is at least about 50% to 150% higher than the first portion.

10. The method according to claim 1, wherein the thread has a radiused surface.

11. The method according to claim 1, wherein the thread has at least three rotations around the chamber with a first height adjacent the opening, a third height adjacent the bottom, and a second height between the first height and second height; wherein the third height is greater than the second height, which is greater than the first height.

12. The method according to claim 1, wherein:

the body comprises an exterior wall; and an annular gap is defined between the chamber and the exterior wall, the annular gap extending axially between the opening and the bottom.

13. The method according to claim 12, wherein the annular gap is configured to accommodate flexing of the chamber.

14. A method of making a cap for removable attachment to an open female luer device, the method comprising:

providing a mold comprising at least a first side and a second side, the first side comprising a mold core for forming a thread;

injecting a liquid polymer into the mold;

allowing the polymer to cool so as to form the cap; and after forming the cap, separating the first and second sides of the mold without rotating the first side;

wherein the cap comprises:

a body comprising an opening, a bottom, and a chamber defined between the opening and the bottom;

a wall of the chamber comprising the thread originating proximate the opening and extending into the chamber, at least a portion of the thread having a height that increases as a function of increasing distance from the opening;

a male post in the chamber projecting from the bottom towards the opening of the body, wherein the male post is spaced from the wall;

a movable piston comprising:

a central opening surrounding the male post;

a top region extending from the central opening and comprising a sealing surface; and a flexible circumferential skirt extending laterally from the movable piston at an acute angle relative to the male post, wherein the skirt is a flange with a gap between the flange and the top region, wherein the flange is in slidable contact with the wall of the chamber;

the method further comprising introducing a liquid disinfectant into the chamber between the bottom of the body and the movable piston.

* * * * *